(12) United States Patent
Ochi et al.

(10) Patent No.: US 10,330,591 B2
(45) Date of Patent: Jun. 25, 2019

(54) FOOD-ARTICLE ANALYSIS DEVICE

(71) Applicant: Panasonic Intellectual Property Management Co., Ltd., Osaka (JP)

(72) Inventors: Kazuhiro Ochi, Kyoto (JP); Tatsuya Takahashi, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 30 days.

(21) Appl. No.: 15/102,777

(22) PCT Filed: Nov. 26, 2014

(86) PCT No.: PCT/JP2014/005927
§ 371 (c)(1),
(2) Date: Jun. 8, 2016

(87) PCT Pub. No.: WO2015/092980
PCT Pub. Date: Jun. 25, 2015

(65) Prior Publication Data
US 2016/0313238 A1 Oct. 27, 2016

(30) Foreign Application Priority Data
Dec. 18, 2013 (JP) ................. 2013-261688

(51) Int. Cl.
*G01J 3/42* (2006.01)
*G01N 21/31* (2006.01)
(Continued)

(52) U.S. Cl.
CPC .............. *G01N 21/314* (2013.01); *G01J 3/42* (2013.01); *G01J 3/427* (2013.01); *G01J 3/453* (2013.01);
(Continued)

(58) Field of Classification Search
CPC .................................................... G01N 21/314
See application file for complete search history.

(56) References Cited

U.S. PATENT DOCUMENTS

| 2007/0218174 A1 | 9/2007 | Hanamatsu et al. |
| 2012/0135384 A1 | 5/2012 | Nakao |
| 2013/0229646 A1* | 9/2013 | Sakurai ............... G01J 3/45 356/51 |

FOREIGN PATENT DOCUMENTS

| JP | 2002-032487 A | 1/2002 |
| JP | 2005-292128 A | 10/2005 |

(Continued)

OTHER PUBLICATIONS

Notification of Reasons for Refusal issued in corresponding Japanese Patent Application No. 2013-261688, dated May 9, 2017; with English translation.

(Continued)

*Primary Examiner* — Michael C Bryant
(74) *Attorney, Agent, or Firm* — McDermott Will & Emery LLP

(57) ABSTRACT

This food-article analysis device is provided with a light-reception/detection unit that receives near-infrared light reflected off of at least one measurement region of a measurement target and/or near-infrared light that has passed through at least one measurement region of said measurement target and generates a signal corresponding to the intensity of the received light, a computation unit that computes sectional nutrition information containing information regarding the caloric content of at least one measurement region and/or information regarding the components thereof on the basis of the signal supplied by the light-reception/detection unit and generates a distribution image by combining a plurality of pieces of sectional nutrition information relating to a plurality of measurement (Continued)

regions with position information for said measurement regions, and a display unit that displays the distribution image supplied by the computation unit.

10 Claims, 10 Drawing Sheets

(51) Int. Cl.
 *G01J 3/453* (2006.01)
 *G01J 3/427* (2006.01)
 *G01N 33/02* (2006.01)
 *G01N 21/359* (2014.01)
(52) U.S. Cl.
 CPC ........... *G01N 21/359* (2013.01); *G01N 33/02* (2013.01); *G01N 2021/3137* (2013.01); *G01N 2021/3166* (2013.01); *G01N 2201/129* (2013.01)

(56) References Cited

FOREIGN PATENT DOCUMENTS

| | | |
|---|---|---|
| JP | 2006-105655 A | 4/2006 |
| JP | 2012-113627 A | 6/2012 |
| JP | 2013-181912 A | 9/2013 |

OTHER PUBLICATIONS

K. Aizawa et al., "Foodlog for Smartphone", IEICE Technical Report, vol. 113, No. 214, Sep. 5, 2013, pp. 67-70, with English abstract and partial English translation.
International Search Report issued in Application No. PCT/JP2014/005927 dated Jan. 6, 2015, with English translation.
English translation of International Preliminary Report on Patentability, issued in corresponding International Patent Application No. PCT/JP2014/005927, dated Jun. 21, 2016.

* cited by examiner

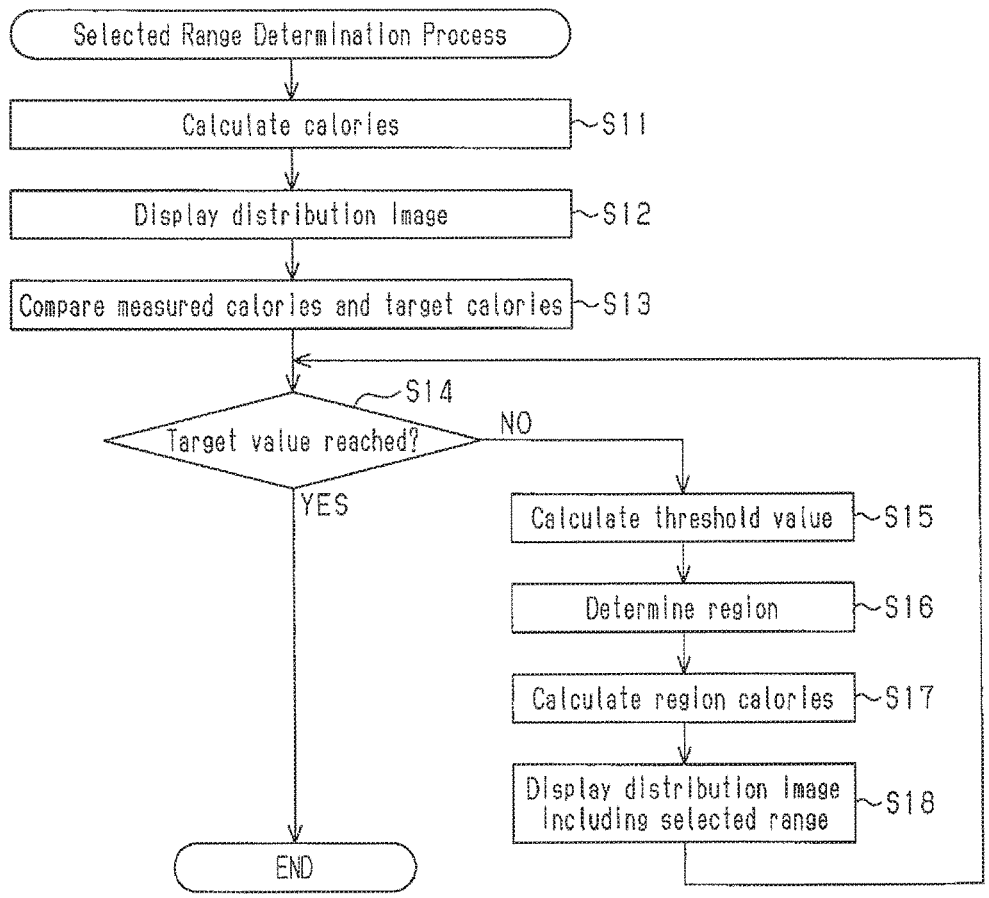
Fig. 15
Fig. 16A
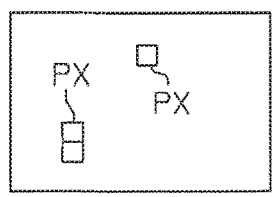
Fig. 16B
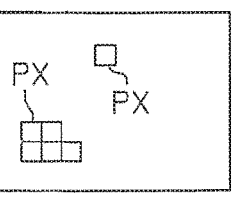
Fig. 16C
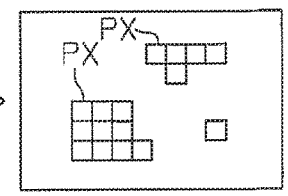

| | | Measured Sugar Amount | Assumed Necessary Insulin Amount | Blood Sugar Value | Intake Insulin | Coefficient |
|---|---|---|---|---|---|---|
| 8:00 | Breakfast 1 | 50g | 6 | 70→110 | 6 | 5.2 [mg/g] |
| 10:30 | Breakfast 2 | 80g | 10 | 60→115 | 10 | 5.5 [mg/g] |
| 12:00 | Lunch 1 | 80g | 9 | 70→120 | 9 | 5.6 [mg/g] |
| 13:30 | Lunch 2 | 80g | 7 | 65→120 | 7 | 7.0 [mg/g] |
| 15:30 | Snack | 60g | 6 | 75→110 | 8 | 4.9 [mg/g] |
| 18:00 | Dinner 1 | 50g | 8 | 70→110 | 8 | 5.0 [mg/g] |
| 20:00 | Dinner 2 | 60g | 8 | 65→110 | 8 | 5.1 [mg/g] |

FOOD-ARTICLE ANALYSIS DEVICE

RELATED APPLICATIONS

This application is the U.S. National Phase under 35 U.S.C. § 371 of International Application No. PCT/JP2014/005927, filed on Nov. 26, 2014, which in turn claims the benefit of Japanese Application No. 2013-261688, filed on Dec. 18, 2013, the disclosures of which are incorporated by reference herein.

TECHNICAL FIELD

The present invention relates to a foodstuff analysis device that analyzes a measurement subject.

BACKGROUND ART

Patent document 1 describes one example of a conventional foodstuff analysis device. The foodstuff analysis device calculates the entire calories of one or more foodstuffs, which are a measurement subject, in a non-destructive manner.

PRIOR ART DOCUMENT

Patent Document

Patent Document 1: Japanese Laid-Open Patent Publication No. 2006-105655

SUMMARY OF THE INVENTION

Problems that are to be Solved by the Invention

The foodstuffs, which are the measurement subject, have different calories and components. Additionally, in each foodstuff, calorie distribution and component distribution are often uneven. Thus, for example, when the entire calories and component amounts of the measurement subject are greater than targets of the user, the user cannot easily recognize which component of the measurement subject should be targeted and how much of it should be adjusted to be proximate to the target.

It is an object of the present invention to provide a foodstuff analysis device that allows the user to easily recognize calorie distribution or component distribution of a measurement subject.

Means for Solving the Problem

One aspect of the present invention is a foodstuff analysis device that includes a light reception detector, a calculation unit, and a display. The light reception detector receives at least one of near-infrared light reflected from at least one measurement portion of a measurement subject and near-infrared light transmitted through at least one measurement portion of the measurement subject and generates a signal corresponding to a light amount of received light. The calculation unit calculates portion nutrition information that includes at least one of information related to calories of at least one measurement portion and information related to a component of at least one measurement portion based on the signal provided from the light reception detector and forms a distribution image by combining each of pieces of portion nutrition information corresponding to measurement portions with position information of the corresponding measurement portion. The display shows the distribution image provided from the calculation unit.

Effect of the Invention

The foodstuff analysis device allows the user to easily recognize calorie distribution or component distribution of a measurement subject.

BRIEF DESCRIPTION OF THE DRAWINGS

FIG. 15 is a flowchart showing the procedures of a selected range determination process that is executed by a calculation unit of a seventh embodiment.

FIGS. 16A-16C are diagrams showing the procedures of a region determination process of the selected range determination process of the seventh embodiment.

EMBODIMENTS OF THE INVENTION

First Embodiment

Figure 1:
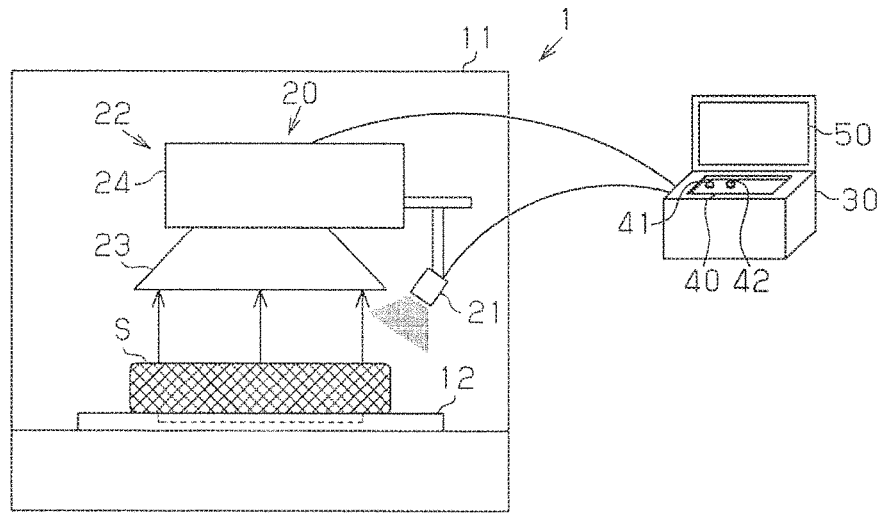
FIG. 1 is a schematic diagram showing the entire structure of a first embodiment of a foodstuff analysis device.

The structure of a foodstuff analysis device 1 will now be described with reference to FIG. 1.

The foodstuff analysis device 1 includes a case 11, a table 12, a measurement unit 20, a calculation unit 30, an operation unit 40, and a display 50.

The table 12 and the measurement unit 20 are located in the case 11. A measurement subject S is placed on the table 12. The foodstuff analysis device 1 is capable of analyzing one or more foodstuffs as the measurement subject S. The foodstuff analysis device 1 is also capable of analyzing a foodstuff located inside a container as the measurement subject S.

The measurement unit 20 includes a light source 21, which emits light to the measurement subject S placed on the table 12, and a light reception unit 22, which receives light reflected from the measurement subject. S.

The light source 21 is located at a position where light can be emitted to the entire measurement subject S. The light emitted from the light source 21 includes at least some wavelengths of near-infrared light having wavelengths of 700 nm to 2500 nm. Examples of the light source 21 include a halogen lamp, an LED, a laser, and the like.

Figure 2:
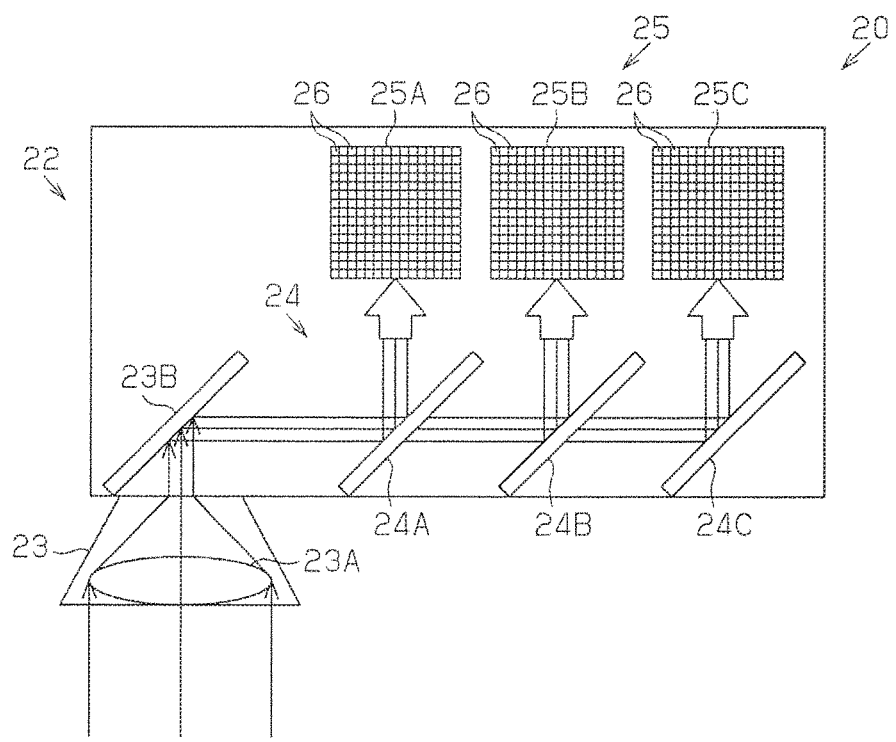
FIG. 2 is a schematic diagram showing the structure of a light reception unit of the first embodiment.

The structure of the light reception unit 22 will now be described with reference to FIG. 2.

The light reception unit 22 includes a light collection portion 23, a particular wavelength reflection unit 24, and a light reception sensor 25. The light reception unit 22 is located at a position where light reflected from the measurement subject S can be received. Shorter distances are preferred between the light reception unit 22 and the measurement subject S.

The light collection portion 23 includes a condenser lens 23A and a reflector 23B.

The particular wavelength reflection unit 24 includes a first reflector 24A, a second reflector 24B, and a third reflector 24C. The reflectors 24A to 24C are each configured as a wavelength selection filter that reflects light having particular wavelengths and transmits light having other wavelengths. The first reflector 24A reflects light having first particular wavelengths and transmits light having other wavelengths. The second reflector 24B reflects light having second particular wavelengths and transmits light having other wavelengths. The third reflector 24C reflects light having third particular wavelengths and transmits light having other wavelengths.

The first to third particular wavelengths are determined, for example, based on spectrum information of foodstuffs having known components through experiments or the like. More specifically, based on the relationship between a particular component ratio and absorbance foodstuffs, wavelengths that well reflect the particular component ratio of the foodstuffs are determined to be the particular wavelengths.

Wavelengths that well correlate with protein, which is a component, are used as the first particular wavelengths. The first particular wavelengths may include, for example, a wavelength of 910 nm and proximate wavelengths. Wavelengths that well correlate with fat, which is a component, are used as the second particular wavelengths. The second particular wavelengths may include, for example, a wavelength of 930 nm and proximate wavelengths. Wavelengths that well correlate with carbohydrate, which is a component, are used as the third particular wavelengths. The third particular wavelengths may include, for example, a wavelength of 980 nm and proximate wavelengths.

The light reception sensor 25 includes light reception elements 26, which are arranged in a lattice. The light reception sensor 25 is configured as an image sensor. The light reception elements 26 may include elements capable of converting a light amount of light to an electric signal, for example, using silicon and indium gallium arsenide, which are widely sensitive to a near-infrared region. The light reception elements 26 correspond to a "light reception detector."

The electric configuration of the foodstuff analysis device 1 will now be described with reference to FIG. 1.

The operation unit 40 includes a measuring button 41 and a switching button 42. When the measuring button 41 is pressed, the operation unit 40 provides the calculation unit 30 with a signal indicating that the measuring button 41 is pressed. When the switching button 42 is pressed, the operation unit 40 provides the calculation unit 30 with a signal indicating that the switching button 42 is pressed.

When receiving the signal indicating that the measuring button 41 is pressed, the calculation unit 30 controls the measurement unit 20 to start an analysis of the measurement subject S. When receiving the signal indicating that the switching button 42 is pressed, the calculation unit 30 changes contents shown on the display 50.

The light paths and the operation of the measurement unit 20 when analyzing the measurement subject will now be described with reference to FIG. 2.

The calculation unit. 30 has the light source 21 (refer to FIG. 1) instantaneously emit light including near-infrared light to the measurement subject S. The light diffused and reflected from the measurement subject S is collected by the condenser lens 23A and received by the reflector 23B as parallel light.

The reflector 23B reflects the received light toward the particular wavelength reflection unit 24. The particular wavelength reflection unit 24 receives the light.

Of the light received by the particular wavelength reflection unit 24, the first reflector 24A reflects light having the first particular wavelengths toward a first light reception sensor 25A and transmits light having other wavelengths. Thus, the light received by the particular wavelength reflection unit 24 and having wavelengths other than the first particular wavelengths is received by the second reflector 24B.

Of the light received by the second reflector 24B, the second reflector 24B reflects light having the second particular wavelengths toward a second light reception sensor 25B and transmits light having other wavelengths. Thus, the light received by the second reflector 24B and having wavelengths other than the second particular wavelengths is received by the third reflector 24C.

Of the light received by the third reflector 24C, the third reflector 24C reflects light having the third particular wavelengths toward a third light reception sensor 25C and transmits light having other wavelengths.

Light beams included in the light directed toward each of the light reception sensors 25A to 25C maintain the position relationship of light beams that were included in light immediately after being diffused and reflected from the measurement subject S. Thus, an output of each light reception element 26 reflects protein, fat, and carbohydrate included in a portion of the measurement subject. More specifically, each light reception element 26 provides the calculation unit 30 (refer to FIG. 1) with a signal that reflects protein, fat, and carbohydrate included in a portion of the measurement subject S (hereafter, referred to as "measurement portion") that is the originating point of light beams received by the light reception element 26.

The calculation unit 30 calculates the ratio and amount of protein based on outputs of the light reception elements 26 of the first light reception sensor 25A and a relational expression stored in advance. The calculation unit 30 calculates the ratio and amount of fat based on outputs of the light reception elements 26 of the second light reception sensor 25B and a relational expression stored in advance. The calculation unit 30 calculates the ratio and amount of carbohydrate based on outputs of the light reception elements 26 of the third light reception sensor 25C and a relational expression stored in advance. Each relational expression may be determined in advance, for example, based on the relationship between the absorbance (light amount) of each wavelength of foodstuffs having known components and the ratio of each component using a PLS process.

Calories of a foodstuff are obtained by multiplying the protein amount, the fat amount, and the carbohydrate amount by the corresponding calorie coefficient and adding the multiplications. Thus, the calculation unit 30 calculates calories of each measurement portion based on the protein amount, the fat amount, and the carbohydrate amount. In each measurement portion, the protein ratio, the protein amount, the fat ratio, the fat amount, the carbohydrate ratio, the carbohydrate amount, and the calories correspond to "portion nutrition information."

The positions of the light reception elements 26 in the light reception sensor 25 correspond to the positions of the measurement portions. The calculation unit 30 forms distribution image information including the positions of the light reception elements 26 and pieces of portion nutrition information associated with the corresponding light reception elements 26.

The calculation unit 30 forms pieces of distribution image information related to calories and components. The calculation unit 30 provides the distribution image information to the display 50. The display 50 shows a distribution image P indicating the distribution image information. The calculation unit 30 also selectively provides distribution image information related to calories and distribution image information related to components to the display 50 based on an output of the operation unit 40.

Figure 3:
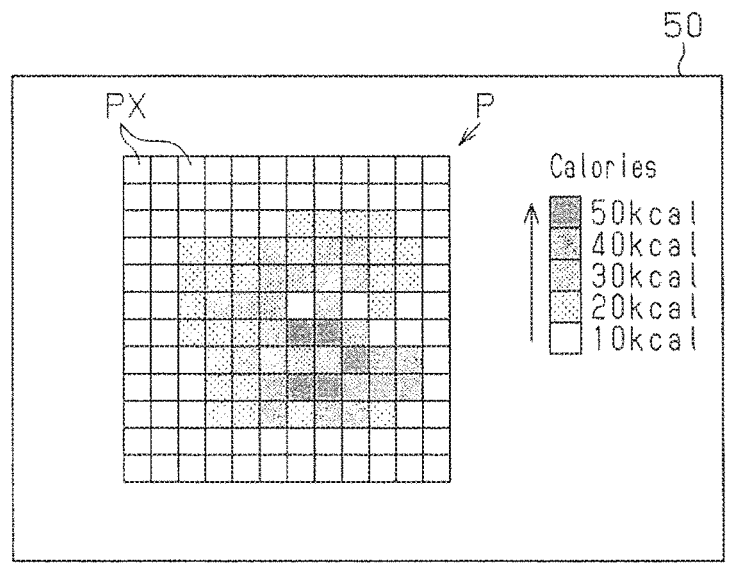
FIG. 3 is a front view showing an example of a calorie distribution image shown on a display of the first embodiment.
Figure 4:
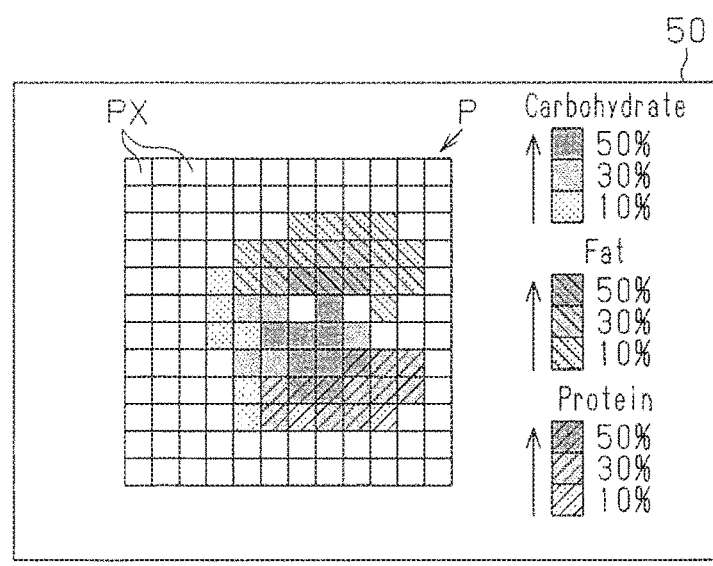
FIG. 4 is a front view showing an example of a component distribution image shown on the display of the first embodiment.

The distribution image P will now be described with reference to FIGS. 3 and 4. In FIGS. 3 and 4, the darkness of each presentation color is indicated by the concentration of dots in a dot hatching. In FIG. 4, the differences of the presentation colors are indicated by line hatchings and directions of lines.

As shown in FIG. 3, a calorie distribution image P is divided into portion regions PX. The distribution image P is divided into, for example, a lattice of the portion regions PX. One portion region PX indicates one piece of portion nutrition information. The position relationship among the portion regions PX conforms to the position relationship among the measurement portions. The calculation unit 30 shows the portion nutrition information obtained from each measurement portion on the corresponding portion region PX of the display 50.

The calorie distribution image P visually presents the amount of calories of each portion region PX in correspondence with the darkness of the presentation color of the portion region PX.

As shown in FIG. 4, a component distribution image P visually presents a component having the largest ratio among protein, fat, and carbohydrate in each portion region PX in a different presentation color. Additionally, the darkness of the presentation color of each portion region PX corresponds to the ratio of the component. This visually presents the ratio of the component in each portion region PX.

The operation of the foodstuff analysis device 1 will now be described.

It is assumed that the measurement subject S is analyzed by a hypothetical foodstuff analysis device that indicates the entire calories and component amounts of the measurement subject S in numeral values. In this case, when the calories or component amounts of the measurement subject S are greater than desired calories or components, the user needs to remove a portion of the measurement subject S and analyze again using the hypothetical foodstuff analysis device. This increases the burden to the user.

The foodstuff analysis device 1 shows the distribution image P on the display 50. Thus, the user easily recognizes the calories and component amounts of the measurement subject S. When the calories or component amounts of the measurement subject S are greater than the desired calories or component amounts, the user easily recognizes which portion of the measurement subject S and how much of it should be removed to obtain the target calories or component amounts. This increases the convenience for the user. Additionally, the target calories or component amounts may be obtained in a short time. This limits changes in taste, form, or the like of the foodstuff, for example, resulting from a temperature change that occurs when the adjustment of the measurement subject S takes time.

In a hypothetical foodstuff analysis device indicating the entire calories and component amounts of the measurement subject S in numeral values, for example, when a number of foodstuffs are analyzed, the user repeats the analysis for each foodstuff. This increases the burden to the user.

The foodstuff analysis device 1 shows the distribution image P on the display 50. Thus, the calories and component amounts of each foodstuff may be recognized by a single measurement. This increases the convenience for the user.

The foodstuff analysis device 1 of the present embodiment has the advantages described below.

(1) The foodstuff analysis device 1 shows the distribution image P on the display 50. Thus, the user easily recognizes the distribution of the portion nutrition information that includes the calories and component amounts of the measurement subject S.

(2) The foodstuff analysis device 1 includes a plurality of light reception elements 26. The calculation unit 30 calculates one piece of the portion nutrition information based on the output of one light reception element 26. This allows the calculation unit 30 to calculate the entire portion nutrition information of the measurement subject S in a short time as compared to a configuration in which the measurement portion is sequentially moved.

(3) The foodstuff analysis device 1 instantaneously emits light from the light source 21. This limits the measurement subject S from changing, for example, being warmed or denatured by the light.

(4) The foodstuff analysis device 1 analyzes the measurement subject S in a non-destructive manner. Thus, the measurement subject S may be used after the measurement.

(5) The foodstuff analysis device 1 analyzes the measurement subject S using near-infrared light. Thus, the foodstuff analysis device 1 may perform the analysis without using equipment such as a centrifuge, a reagent, and the like that are used when the measurement subject S is crushed and chemically analyzed.

Second Embodiment

A second embodiment of the foodstuff analysis device differs from the first embodiment of the foodstuff analysis device 1 in that a number of measurement portions are sequentially measured. The second embodiment and the first embodiment have the same structure in other components. In the description of the foodstuff analysis device 1 of the second embodiment, the same reference characters are given to those components that are the same as the corresponding components of the foodstuff analysis device 1 of the first embodiment.

The structure of the foodstuff analysis device 1 will now be described with reference to FIGS. 5 and 6.

Figure 5:
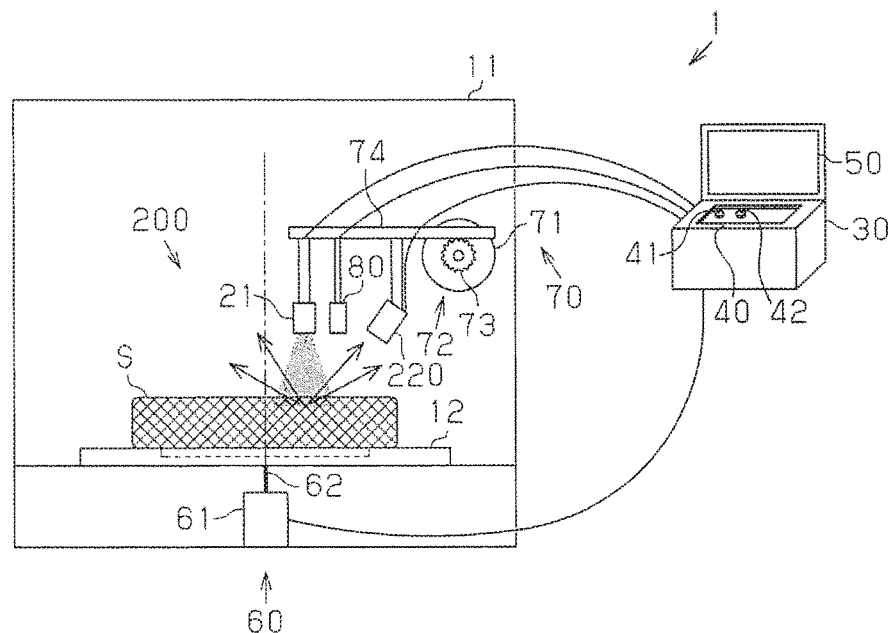
FIG. 5 is a schematic diagram showing the entire structure of a second embodiment of a foodstuff analysis device.
Figure 6:
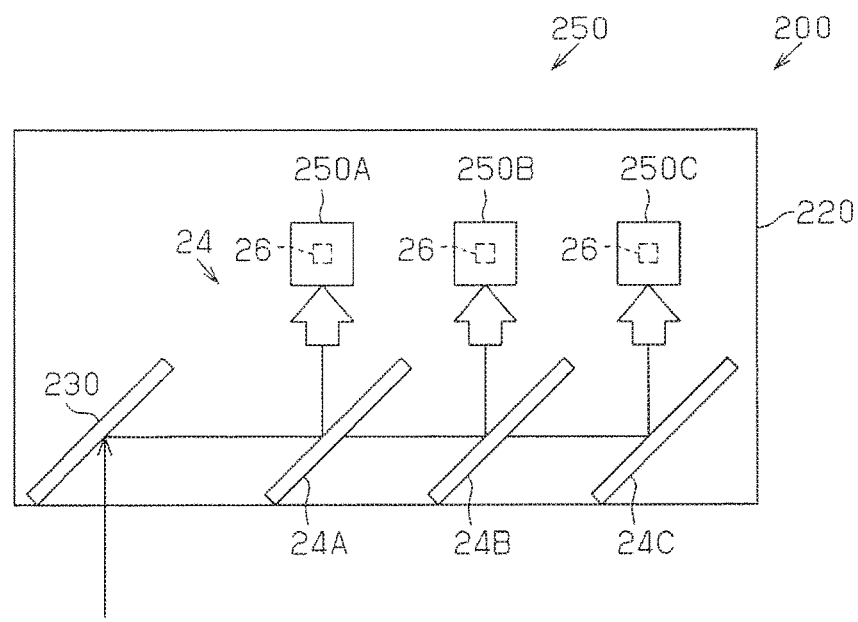
FIG. 6 is a schematic diagram showing the structure of a light reception unit of the second embodiment.

As shown in FIG. 5, the foodstuff analysis device 1 includes the case 11, the table 12, a measurement unit 200, the calculation unit 30, the operation unit 40, the display 50, a table driver 60, a measurement unit driver 70, and a distance detector 80.

The table driver 60 supports the table 12 from below. The table driver 60 includes a motor 61 and a rotation shaft 62. The rotation shaft 62 connects the center of the table 12 and the motor 61. When the motor 61 is driven, the table 12 is rotated about the rotation shaft 62 (hereafter, referred to as circumferentially).

The measurement unit driver 70 includes a motor 71 and a slide mechanism 72. The slide mechanism 72 includes a pinion gear 73 and a rack 74. The rack 74 extends in a radial direction of the table 12 above the table 12. The light source 21, a light reception unit 220, and the distance detector 80 are suspended from the rack 74. The pinion gear is connected to the motor 71 and meshed with teeth of the rack 74.

When the driving of the motor 71 rotates the pinion gear 73, the rack 74 is moved in the radial direction of the table 12 above the table 12. Thus, in accordance with the movement of the rack 74, the light source 21 of the measurement unit 200 and the light reception unit 220 of the measurement unit 200 move in the radial direction of the table 12 above the table 12.

The distance detector 80 is located close to the light reception unit 220. The distance detector 80 provides the calculation unit 30 with a signal corresponding to the distance to the measurement subject S. The distance detector 30 may include a distance sensor that uses light, an ultrasonic wave, or the like. Alternatively, the distance detector 80 may include a detection device that detects a focal length using a lens or the like.

The structure of the light reception unit 220 will now be described with reference to FIG. 6.

The light reception unit 220 includes a reflector 230, the particular wavelength reflection unit 24, and light reception sensors 250. Each light reception sensor 250 includes one light reception element 26.

The operation of the foodstuff analysis device 1 when analyzing the measurement subject S will now be described with reference to FIGS. 5 and 6.

As shown in FIG. 5, the calculation unit 30 has the light source 21 instantaneously emit light including near infrared light to the measurement subject S. As shown in FIG. 6, light diffused and reflected from the measurement subject S is received by the reflector 230.

The reflector 230 reflects the received light toward the particular wavelength reflection unit 24. The particular wavelength reflection unit 24 receives the light.

Of the light, received by the particular wavelength reflection unit 24, the first reflector 24A reflects light having the first particular wavelengths toward a first light reception sensor 250A and transmits light having other wavelengths to the second reflector 24B.

Of the light received by the second reflector 24B, the second reflector 24B reflects light having the second particular wavelengths toward a second light reception sensor 250B and transmits light having other wavelengths to the third reflector 24C.

Of the light received by the third reflector 24C, the third reflector 24C reflects light having the third particular wavelengths toward a third light reception sensor 250C and transmits light having other wavelengths.

Light directed toward each of the light reception sensors 250A to 250C is the light that has been reflected from a portion of the measurement subject S (measurement portion) opposed to the reflector 230. Thus, outputs of the light reception elements 26 reflect protein, fat, and carbohydrate of the measurement portion. More specifically, each light reception element 26 provides the calculation unit 30 with a signal that reflects protein, fat, or carbohydrate of the measurement portion. The distance detector 80 provides the calculation unit 30 with a signal corresponding to the distance to the measurement portion.

The calculation unit 30 calculates the ratio and amount of protein based on the output of the light reception element 26 of the first light reception sensor 250A and a relational expression stored in advance. The calculation unit 30 calculates the ratio and amount of fat based on the output of the light reception element 26 of the second light reception sensor 250B and a relational expression stored in advance. The calculation unit 30 calculates the ratio and amount of carbohydrate based on the output of the light reception element 26 of the third light reception sensor 250C and a relational expression stored in advance.

The calculation unit 30 also calculates the thickness of the measurement portion based on the output of the distance detector 80 and corrects the calculated protein amount, fat amount, and carbohydrate amount. More specifically, the calculation unit 30 increases correction amounts of protein, fat, and carbohydrate when the measurement portion is thicker and decreases correction amounts of protein, fat, and carbohydrate when the measurement portion is thinner.

When the measuring button 41 is pressed, the calculation unit 30 controls the table driver 60 and the measurement unit driver 70 to sequentially change the measurement portion in accordance with the following procedures.

Figures 7A, 7B, 7C:
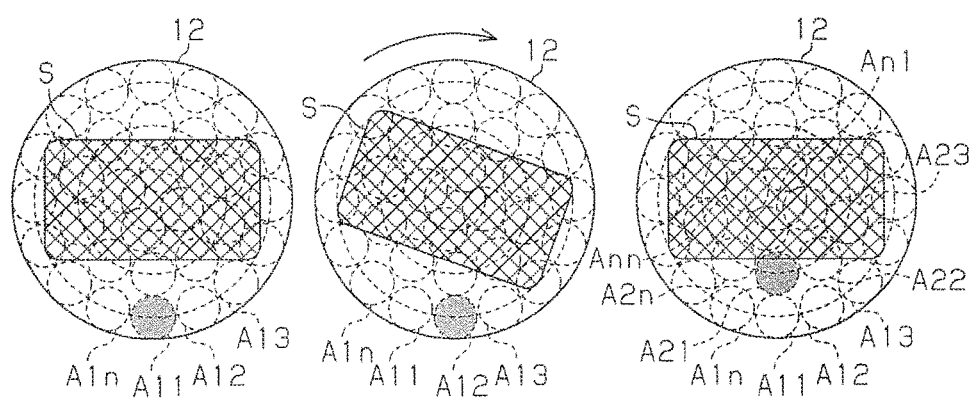
FIG. 7A is an operation diagram showing the procedures for measuring a measurement subject in the second embodiment.
FIG. 7B is an operation diagram showing that rotation of the table has moved the measurement region to a region that is circumferentially adjacent to the measurement region of FIG. 7A.
FIG. 7C is an operation diagram showing that movement of the measurement unit has moved the measurement region to a region that is radially adjacent to the measurement region of FIG. 7A.

(procedure 11) As shown in FIG. 7A, the calculation unit 30 sets the measurement portion to a measurement region A11 and moves the reflector 230 to a position above the measurement region A11. The calculation unit 30 calculates the portion nutrition information of the measurement region A11.

(procedure 12) As shown in FIG. 7B, the calculation unit 30 has the table driver 60 rotate the table 12 so that the measurement portion is changed from the measurement region A11 to a measurement region A12 that is circumferentially adjacent to the measurement region A11. The calculation unit 30 calculates the portion nutrition information of the measurement region A12.

(procedure 13) The calculation unit 30 calculates the portion nutrition information of each of measurement regions A11 to A1n as rotating the table 12 by a predetermined amount at a time. More specifically, the calculation unit 30 calculates the portion nutrition information along the entire circumference of the table 12.

(procedure 14) As shown in FIG. 7C, the calculation unit 30 has the measurement unit driver 70 move the rack 74. The calculation unit 30 changes the measurement portion from the measurement region A11 to a measurement region A21 that is adjacent to the measurement region A11 in the radial direction of the table 12. The calculation unit 30 calculates the portion nutrition information of the measurement region A21.

The calculation unit 30 repeats (procedure 11) to (procedure 14) to calculate the portion nutrition information over the entire table 12. The calculation unit 30 forms distribution image information by combining a measurement portion and the portion nutrition information that has been calculated based on the outputs of the light reception elements 26 corresponding to the measurement portion. More specifically, the calculation unit 30 selects a measurement portion from the rotation angle of the table 12 and the radial position information of the measurement unit 200 and combines the selected measurement portion and the portion nutrition information analyzed in the measurement portion. When pieces of portion nutrition information are calculated over the entire table 12, the calculation unit 30 forms the distribution image information by respectively combining a number of measurement portions and the pieces of portion nutrition information analyzed in the measurement portions. The calculation unit 30 provides the distribution image information to the display 50. The display 50 shows a distribution image P indicating the distribution image information.

Figure 8:
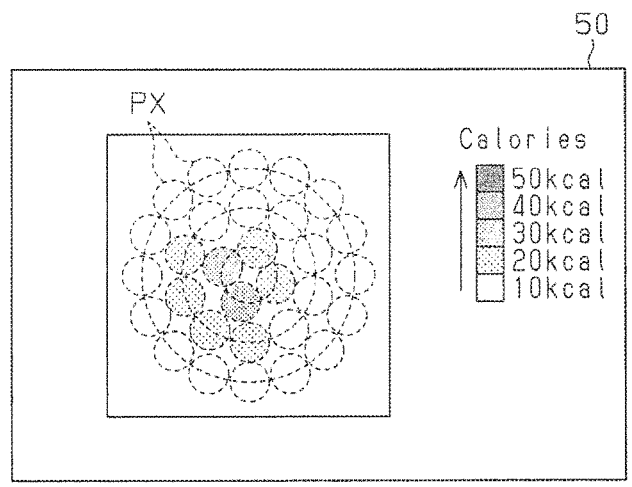
FIG. 8 is a front view showing an example of a calorie distribution image shown on a display of the second embodiment.

As shown in FIG. 8, the distribution image P is divided into portion regions PX corresponding to the movement pattern of the measurement unit 200 relative to the table 12. One portion region PX indicates one piece of portion nutrition information.

The second embodiment of the foodstuff analysis device 1 has the advantages described below in addition to (1) and (3) to (5) of the first embodiment.

(6) The foodstuff analysis device 1 relatively moves the measurement unit 200 and the measurement subject S. This reduces the number of light reception elements 26.

(7) The foodstuff analysis device 1 includes the distance detector 80. Thus, the foodstuff analysis device 1 is capable of detecting the thickness of the measurement portion of the measurement subject S. This increases the accuracy for calculating the protein amount, the fat amount, and the carbohydrate amount.

Third Embodiment

A third embodiment of the foodstuff analysis device 1 differs from the second embodiment of the foodstuff analysis device 1 in that the foodstuff analysis device 1 changes the number of measurement portions based on outputs of the light reception elements 26. The third embodiment and the second embodiment have the same structure in other components. In the description of the foodstuff analysis device 1 of the third embodiment, the same reference characters are given to those components that, are the same as the corresponding components of the foodstuff analysis device 1 of the second embodiment.

The procedures for measuring the measurement portion will now be described with reference to FIGS. 7 to 9.

The calculation unit 30 controls the table driver 60 and the measurement unit driver 70 to sequentially change the measurement portions in accordance with the following procedures.

(procedure 21) As shown in FIG. 7A, the calculation unit 30 sets the measurement portion to the measurement region A11 and moves the reflector 230 to a position above the measurement region A11. The calculation unit 30 calculates the portion nutrition information of the measurement region A11.

(procedure 22) The calculation unit 30 has the table driver 60 rotate the table 12 and changes the measurement portion from the measurement region A11 to a measurement region A13. The measurement region A13 and the measurement region A11 are located at circumferentially opposite sides of the measurement region A12.

Figure 9A:
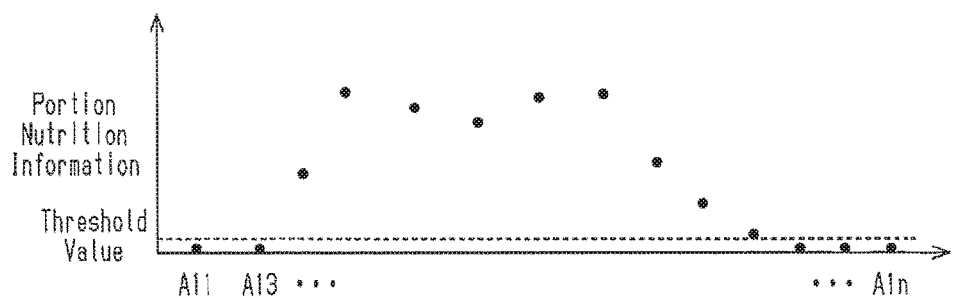
FIG. 9A is a graph showing one example of the relationship between the measurement region and portion nutrition information in the first cycle of the measurement procedures of a third embodiment.
Figure 9B:
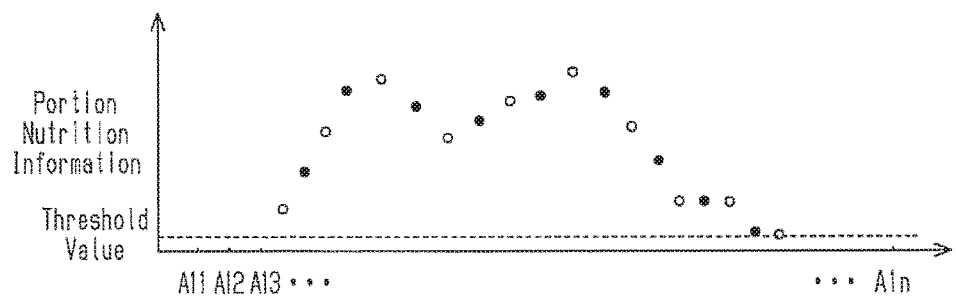
FIG. 9B is a graph showing one example of the relationship between the measurement region and portion nutrition information in the second cycle.

(procedure 23) As shown in FIG. 9A, the calculation unit 30 calculates portion nutrition information of every other measurement regions A11 to A1n along the entire circumference of the table 12 as rotating the table 12 by a predetermined amount at a time.

(procedure 24) The calculation unit 30 determines whether or not all pieces of the portion nutrition information of each of the measurement regions A11 to A1n are greater than a predetermined threshold value. More specifically, the calculation unit 30 determines whether or not the calories, the protein amount, the fat amount, and the carbohydrate amount are all greater than the predetermined threshold value.

(procedure 25) As shown in FIG. 92, the calculation unit 30 measures a measurement region that is adjacent to one of the measurement regions A11 to A1n that has been determined to have at least one piece of the portion nutrition information being greater than the threshold value.

(procedure 26) As shown in FIG. 70, the calculation unit 30 has the measurement unit driver 70 move the rack 74 and changes the measurement portion from the measurement region A11 to the measurement region A21, which is adjacent to the measurement region 11A in the radial direction of the table 12.

The calculation unit 30 also repeats (procedure 21) to (procedure 26) in the measurement regions A21 to A2n. The calculation unit 30 calculates the portion nutrition information in A11 to Ann. The calculation unit 30 forms distribution image information by combining a measurement portion and the portion nutrition information that has been calculated based on outputs of the light reception elements 26 corresponding to the measurement portion.

The third embodiment of the foodstuff analysis device 1 has the advantage described below in addition to (1) and (3) to (7) of the first and second embodiments.

(8) The foodstuff analysis device 1 may reduce the number of measurement portions in accordance with the threshold value. This shortens the overall analysis time of the measurement subject S as compared to a configuration in which all of the measurement regions A11 to Ann are measured.

Fourth Embodiment

A fourth embodiment of the foodstuff analysis device 1 differs from the first embodiment of the foodstuff analysis device 1 in that the measurement unit 20 includes an image obtaining unit 27. The fourth embodiment and the first embodiment have the same structure in other components. In the description of the foodstuff analysis device 1 of the fourth embodiment, the same reference characters are given to those components that are the same as the corresponding components of the foodstuff analysis device 1 of the first embodiment.

Figure 10:
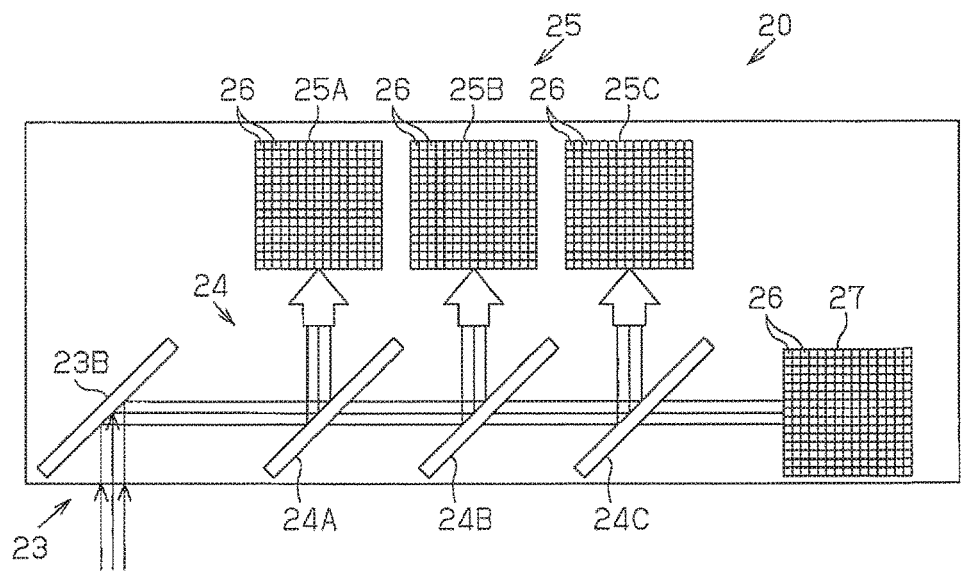
FIG. 10 is a diagram showing the structure of a light reception unit of a fourth embodiment.

As shown in FIG. 10, the light reception unit 22 includes the image obtaining unit 27, which is located at a downstream side of the third reflector 24C.

Of light received by the third reflector 24C, the third reflector 24C reflects light having the third particular wavelengths toward the third light reception sensor 25C and transmits light having other wavelengths to the image obtaining unit 27.

In the image obtaining unit 27, a filter portion (not shown) in which red, green, and blue vapor deposition filters arranged in a lattice is overlapped with a lattice of the light reception elements 26. More specifically, the image obtaining unit 27 captures an image of the measurement subject S using visible light. The calculation unit 30 forms image information of the captured measurement subject S.

Figure 11A:
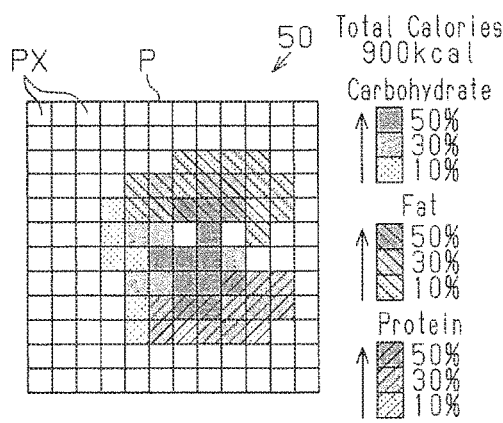
FIG. 11A is a front view showing an example of a calorie distribution image.
Figure 11B:
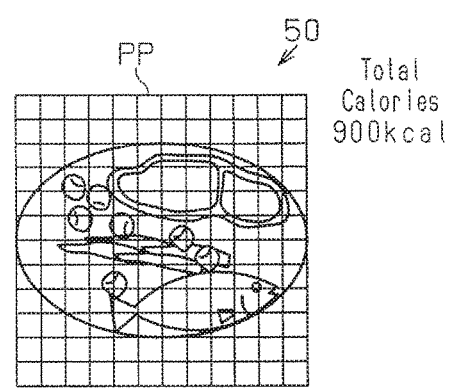
FIG. 11B is a front view showing an example of a picture image.
Figure 11C:
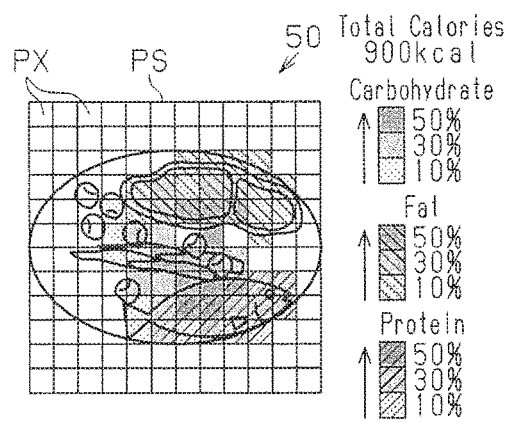
FIG. 11C is a front view showing a superimposed image, each of which is shown on a display of the fourth embodiment.

FIG. 11A shows a distribution image P. FIG. 11B shows a picture image PP that is displayed based on the image information. As shown in FIG. 11C, the calculation unit 30 displays a superimposed image PS in which the distribution image P of FIG. 11A is superimposed on the picture image PP of FIG. 11B. When the switching button 42 is pressed, the calculation unit 30 switches the image on the display 50 among the distribution image P, the picture image PP, and the superimposed image PS.

The fourth embodiment of the foodstuff analysis device 1 has the advantages described below in addition to (1) and (3) to (7) of the first to third embodiments.

(9) The display 50 shows the superimposed image PS including the picture image PP. Thus, the visual information of the measurement subject S, which is recognized by the user, is overlapped with the distribution image P. This facilitates the intuitive recognition of the distribution of the portion nutrition information.

(10) In the superimposed image PS, the picture image PP reproducing visible light and the distribution image P may not be easily distinguished. This may hinder the recognition of the distribution of the portion nutrition information. The foodstuff analysis device 1 is capable of switching between the superimposed image PS and the distribution image P. This limits situations in which the portion nutrition information is not easily recognized.

Fifth Embodiment

A fifth embodiment of the foodstuff analysis device 1 differs from the fourth embodiment of the foodstuff analysis device 1 in that a display 150 is configured as a touch panel and allows a portion of the distribution image P to be selected. The fifth embodiment and the fourth embodiment have the same structure in other components. In the description of the foodstuff analysis device 1 of the fifth embodiment, the same reference characters are given to those components that are the same as the corresponding components of the foodstuff analysis device 1 of the fourth embodiment.

The structure of the display 150 will now be described with reference to FIG. 12.

The display 150 is configured as a touch panel. The display 150 transmits information that is input on the display 150 to the calculation unit 30.

The user may input gender, age, weight, and an activity level from the display 150. The activity level refers to the intensity of average daily life activity and includes a number of stages (e.g., three stages) corresponding to the intensity. Here, gender, age, weight, and the activity level correspond to "designated information." The display 150 corresponds to an "information input unit" and a "selection unit."

The calculation unit 30 calculates a target value of intake calories per day (hereafter, referred to as "target calories") and a target value of intake component amounts per meal (hereafter, referred to as "target component amounts") for the user based on gender, age, weight, and the activity level. The target calories conform to basal metabolism calories of the user. The target component amounts are calculated for each component and include a target protein amount, a target fat amount, and a target carbohydrate amount.

Figure 12:
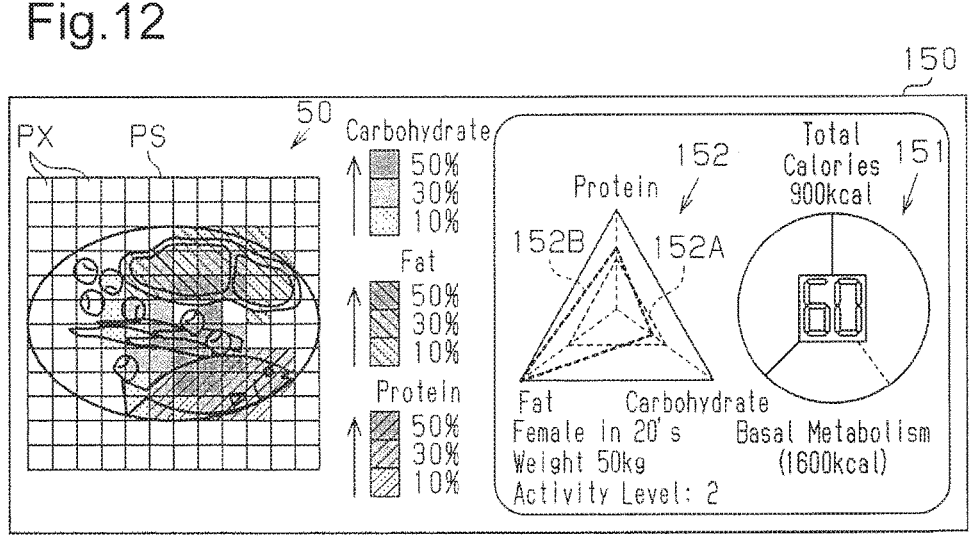
FIG. 12 is a front view showing an example of presentation shown on a display of a fifth embodiment.

As shown in FIG. 12, the calculation unit 30 shows the calories of the measurement subject S and the target calories on a calorie display 151 of the display 150 together with the distribution image P. The calorie display 151 shows the ratio of the calories of the measurement subject S to the target calories by a chart and a percentage numeral value.

The calculation unit 30 shows the component amounts of the measurement subject S and the target component amounts on a component display 152 of the display 150. The component display 152 shows the relationship between the target component amounts and the component amounts of the measurement subject S by a chart. The component display 152 shows, for example, the target protein amount, the target fat amount, and the target carbohydrate amount using a triangular target diagram 152A. The component display 152 also shows a triangular measurement diagram 152B, which indicates the protein amount, the fat amount, and the carbohydrate amount of the measurement subject S. The measurement diagram 152B is overlapped with the target diagram 152A.

In the example shown in FIG. 12, a circle chart and numeral values indicate that the calories of the measurement subject S (900 kcal) is 60% of the target calories (1600 kcal). Additionally, it is indicated that the protein amount of the measurement subject S is slightly greater than the target protein amount, that the fat amount of the measurement subject S is significantly greater than the target fat amount, and that the carbohydrate amount of the measurement subject S is slightly less than the target carbohydrate amount.

The user can select a portion of the distribution image P (hereafter, referred to as "selected range RS") by touching and enclosing the portion of the distribution image P shown on the display 150 using a finger.

Figure 13:
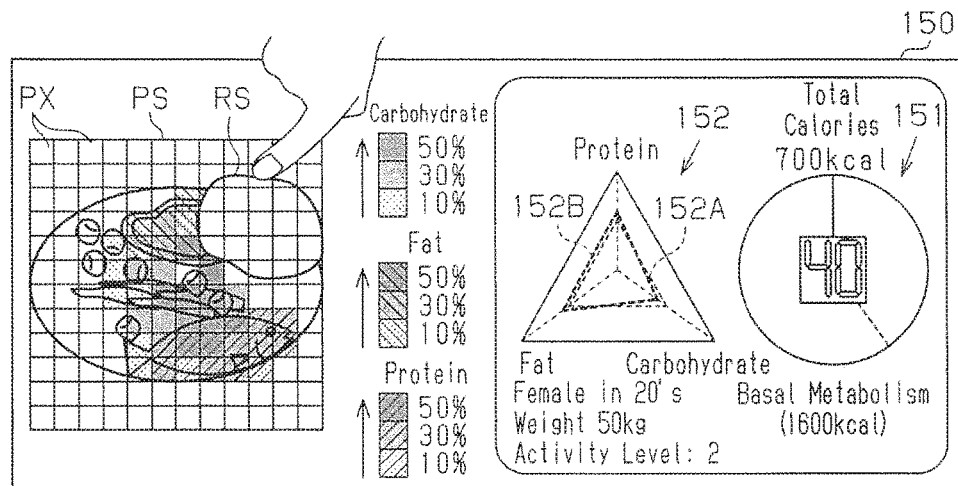
FIG. 13 is a front view showing an example of contents shown on a display of the fifth embodiment when a selected range is input.

As shown in FIG. 13, the user selects a portion of the distribution image P as the selected range RS. The user selects, for example, a portion of the distribution image P including much fat distribution as the selected range RS.

When receiving information in which the selected range RS is set in the distribution image P, the calculation unit 30 calculates calories and a sum of each component amount of the measurement subject. S excluding the selected range RS. The calculation unit 30 calculates a sum of calories and a sum of each component amount of portion regions PX that are not included in the selected range RS. The sum of calories and the sum of each component amount that are not included in the selected range RS correspond to "reference information."

The calculation unit 30 shows the calculated sums of calories and each component amount of portions that are not included in the selected range RS on the display 150.

In the example shown in FIG. 13, a circle chart and numeral values indicate that the calories of the measurement subject S excluding the selected range RS (700 kcal) is decreased to 40% of the target calories (1600 kcal). Additionally, it is indicated that when the selected range RS is excluded, the protein amount of the measurement subject. S generally conforms to the target protein amount, the fat amount of the measurement subject S generally conforms to the target fat amount, and the carbohydrate amount of the measurement subject S is slightly less than the target carbohydrate amount. By viewing the display 150, the user can recognize the intake calories and the intake components when the selected range RS is excluded from the measurement subject.

The fifth embodiment of the foodstuff analysis device 1 has the advantage described below in addition to (1), (3) to (7), (9), and (10) of the first to fourth embodiments.

(11) The foodstuff analysis device 1 shows the sum of calories and the sum of each component amount of portions that are not included in the selected range RS on the display 150. Thus, the user may easily simulate which portion of the measurement subject S and how much of it should be removed to obtain the target calories and the target component amounts. This increases the convenience for the user.

Sixth Embodiment

A sixth embodiment of the foodstuff analysis device 1 differs from the fifth embodiment of the foodstuff analysis device 1 in that foodstuff candidates S1 to Cu that may be substituted by the selected range RS are presented. The sixth embodiment and the fifth embodiment have the same structure in other components. In the description of the foodstuff analysis device 1 of the sixth embodiment, the same reference characters are given to those components that are the same as the corresponding components of the foodstuff analysis device 1 of the fifth embodiment.

The calculation unit 30 stores pieces of portion nutrition information of the measurement subject S that have been analyzed in the past in a memory (not shown).

When at least one of the component amounts of the measurement subject S is greater than the target component amount, the user operates the display 150 and selects the selected range RS.

Figure 14A:
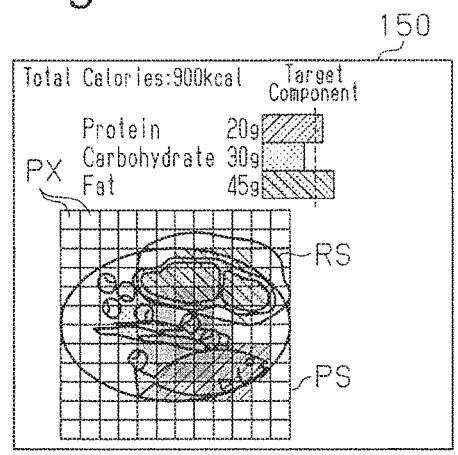
FIG. 14A is a front view showing an example of presentation when a selected range is input.

As shown in FIG. 14A, when the selected range RS is selected, the calculation unit 30 calculates each component amount of the measurement subject S excluding the selected range RS. The calculation unit 30 also shows, on the display 150, numeral values and a bar chart indicating each component amount of the measurement subject S excluding the selected range RS.

The calculation unit 30 calculates the difference between the component amounts that is obtained when the selected range RS is excluded and the target component amounts. From information, of the measurement subjects S that have been analyzed in the past and stored in the memory, the calculation unit 30 selects information of one or more measurement subjects S that are proximate to the difference between the component amounts of the present measurement subject. S and the target component amounts as foodstuff candidates C1 to Cn. The foodstuff candidates C1 to Cn correspond to "substitute presentation information."

Figure 14B:
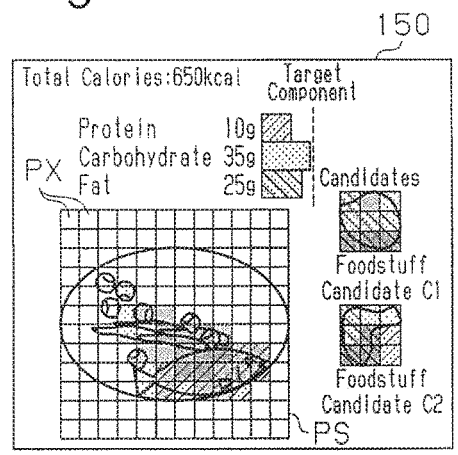
FIG. 14B is a front view showing an example of a foodstuff candidate.

The calculation unit 30 shows the foodstuff candidates C1 to Cn on the display 150. In the example shown in FIG. 14B, the calculation unit 30 shows the foodstuff candidate C1 and the foodstuff candidate C2 on the display 150.

Figure 14C:
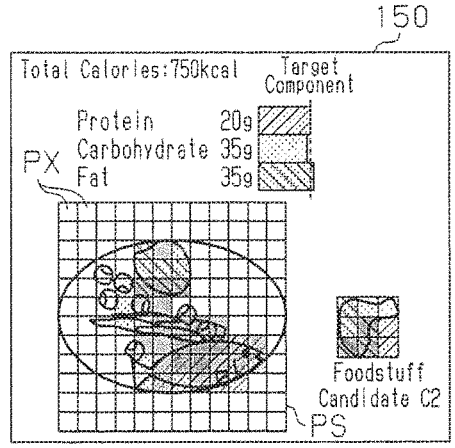
FIG. 14C is a front view showing an example of contents when the user selects a foodstuff candidate, each of which is shown on a display of a sixth embodiment.

For example, as shown in FIG. 14C, when the user operates the display 150 and selects the foodstuff candidate C1, the calculation unit 30 shows a distribution image P in which the selected range RS is replaced by the foodstuff candidate C1 on the display 150. The calculation unit 30 also adds the component amounts of the foodstuff candidate C1 to each component amount of the measurement subject S excluding the selected range RS and shows the added numeral values using the bar chart on the display 150.

The sixth embodiment of the foodstuff analysis device 1 has the advantage described below in addition to (1), (3) to (7), and (9) to (11) of the first to fifth embodiments.

(12) The foodstuff analysis device 1 shows the foodstuff candidates C1 to Cn corresponding to the selected range RS of the measurement subject S or a foodstuff that is selected when the measurement subject S includes a number of foodstuffs. This easily obtains the target component amounts. Thus, the foodstuff analysis device 1 may facilitate the planning of a meal menu or the like.

Seventh Embodiment

A seventh embodiment of the foodstuff analysis device 1 differs from the fifth embodiment of the foodstuff analysis device 1 in that the calculation unit 30 executes a selected range determination process in which the selected range RS is calculated. The seventh embodiment and the fifth embodiment have the same structure in other components. In the description of the foodstuff analysis device 1 of the seventh embodiment, the same reference characters are given to those components that are the same as the corresponding components of the foodstuff analysis device 1 of the fifth embodiment.

The selected range determination process will now be described with reference to FIG. 15. The process is started when the measuring button 41 is pressed.

In step S11, the calculation unit 30 analyzes the measurement subject S and calculates the entire calories (hereafter, referred to as "total calories") of the measurement subject S. In step S12, the calculation unit 30 shows the distribution image P on the display 150. The total calories correspond to "total nutrition information."

In step S13, the calculation unit 30 compares the total calories and the target calories.

In step S14, the calculation unit 30 determines whether or not the total calories conform to the target calories. More specifically, the calculation unit 30 determines whether or not the total calories are the same as or sufficiently close to the target calories. When determined that the total calories conform to the target calories, the calculation unit 30 terminates the present process.

When determined that the total calories do not conform to the target calories, in step S15, the calculation unit 30 determines a threshold value for calories of each piece of portion nutrition information (hereafter, referred to as "portion calories").

In step S16, as shown in FIG. 16A, the calculation unit 30 selects portion regions PX having the portion calories that are higher than the threshold value.

In step S17, the calculation unit 30 calculates a sum of the portion calories of the selected portion regions PS and subtracts the sum from the total calories. In step S18, the calculation unit 30 shows, on the display 150, an image in which the portion regions PX selected in step S16 are shown on a superimposed image PS. The process for showing such portion regions PX is configured to enclose the corresponding portion regions PX with a line, flash the corresponding portion regions PX, or change the presentation color of the corresponding portion regions PX on the superimposed image PS. The image in which the selected portion regions PX are shown on the superimposed image PS corresponds to "suggestion information."

In step S13, the calculation unit 30 again determines whether or not the total calories that have been reduced in step S17 conform to the target calories.

When determined that the total calories do not conform to the target calories, the calculation unit 30 again repeats the processes of step S15 to step S18. In the process of step S15 from the second time and on, the calculation unit 30 sets the threshold value to be less than the previous threshold value. In the process of step S16 from the second time and on, as shown in FIGS. 16B and 16C, the calculation unit 30 selects portion regions PX having a value greater than the threshold value from portion regions PX that are adjacent to the selected portion regions PX.

The seventh embodiment of the foodstuff analysis device 1 has the advantages described below in addition to (1), (3) to (7), and (9) to (11) of the first to sixth embodiments.

(13) The foodstuff analysis device 1 shows the suggestion information, which is for conforming the measurement subject S to the target calories. This may be convenient for the user.

(14) In step S13, the calculation unit 30 selects two adjacent portion regions PX. This decreases the potential of including small regions, which are difficult to be removed.

Other Embodiments

The present foodstuff analysis device includes embodiments other than the first to seventh embodiments. Other embodiments of the present foodstuff analysis device include modified examples of the first to seventh embodiments described below.

In the light reception sensors 25A to 25C of the first embodiment, the circular arrangement of the light reception elements 26 may be changed to a concentric arrangement of the light reception elements 26. Alternatively, the light reception elements 26 may be linearly arranged. When such light reception elements 26 are moved in a direction orthogonal to the linear direction of the light reception elements 26, the light reception elements 26 may be laid out in a pseudo-two dimensional arrangement. In a structure in which the light reception elements 26 are linearly arranged, the irradiation time of the light source 21 is changed in accordance with the movement time of the light reception elements 26.

The calculation unit 30 of the first, embodiment calculates portion nutrition information of one portion region PX based on an output of one light reception element 26. Instead, portion nutrition information of one portion region PX may be calculated based on outputs of adjacent light reception elements 26. In this modified example, the calculation unit 30 may average outputs of adjacent light reception elements 26 and calculate the portion nutrition information of one portion region PX. Alternatively, the portion nutrition information of one portion region PX may be calculated based on the sum of the outputs of the adjacent light reception elements 26. In this case, the number of portion regions PX is reduced. This facilitates the recognition of the entire calories and general component distribution of the measurement subject S.

The distance detector 80 of the second embodiment may be located beside the measurement subject S. In this case, the distance detector 80 is moved in a height-wise direction. The distance detector 80 outputs a signal corresponding to the distance to the measurement subject S in each height-wise position to the calculation unit 30. The calculation unit 30 calculates a general contour of the measurement subject S based on the outputs of the distance detector 80 and estimates the thickness of each measurement portion of the measurement subject S.

The measurement unit driver 70 of the second embodiment moves the light reception unit 220 and the light source 21 relative to the table 12. Instead, while the light source 21 is fixed to the case 11, only the light reception unit 220 may be moved. In this case, the measurement portion may be changed, for example, by changing a light path. More specifically, the measurement unit 200 includes a reflector between the light source 21 and the measurement subject S. Movement and angle change of the reflector relative to the table 12 changes the measurement portion of the measurement subject S that is irradiated with light from the light source 21. The light reception unit 220 sequentially moves to a position where light reflected from the measurement portion is receivable.

The structure of the foodstuff analysis device 1 of the second embodiment may be changed so that the table driver 60 radially moves the table 12 and the measurement unit driver 70 circumferentially rotates the light reception unit 220. Further, one of the table 12 and the light reception unit 220 may be configured to be movable in radial and circumferential directions.

Figure 17A:
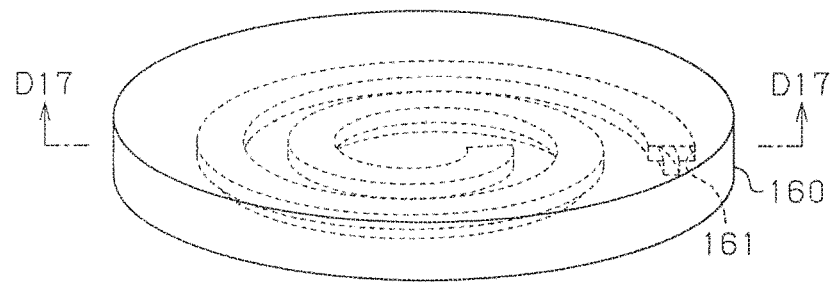
FIG. 17A is a perspective view showing a support base of a modified example of the second embodiment.
Figure 17B:
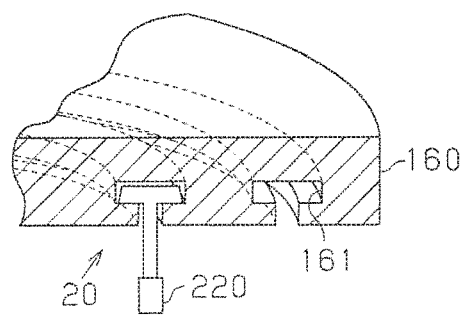
FIG. 17B is a cross-sectional view taken along line D17-D17 in FIG. 17A.

FIG. 17 shows one example of configuration in which the light reception unit 220 radially moves and circumferentially rotates. The light reception unit 220 includes a support base 160 that suspends the light reception unit 220. The support base 160 has a diameter that covers the entire table 12 from above. The lower surface of the support base 160 includes a spiral groove 161. The light reception unit 220 is engaged with the groove 161. The light reception unit 220 is connected to a drive source, for example, by a mechanism such as an articulated arm. When the light reception unit 220 is driven by the drive source and moved on the groove 161, the entire measurement subject S may be analyzed.

Additionally, the table driver 60 may be configured to linearly move the table 12 in a direction different from the direction in which the light reception unit 220 moves relative to the table 12.

Any structure may be used as long as the measurement unit 200 is capable of measuring the entire measurement subject S that is placed on the table 12. In the structure in which only the measurement unit 200 is moved, the measurement subject S may be kept still. Thus, the measurement subject S does not receive force and may not be deformed even when the measurement subject S is liquid or easy to deform. This limits decreases of the measurement accuracy caused by the deformation of the measurement subject S.

The measurement regions A11 to Ann of the second embodiment are arranged so that adjacent ones of the measurement regions A11 to Ann do not overlap with each other. However, adjacent ones of the measurement regions A11 to Ann may be arranged to be overlapped with each other.

In the second embodiment, the measurement regions A11 to Ann are changed whenever the measurement is completed. Instead, the measurement may be performed as rotating the table driver 60. In this case, when the portion regions PX of the distribution image P are further segmentalized, the continuous distribution image P may be shown.

In the measurement regions A11 to Ann of the second embodiment, portion nutrition information between adjacent ones of the measurement regions A11 to Ann may be calculated through an interpolation process. In this case, the number of portion regions PX of the distribution image P increases in accordance with the interpolation process.

Instead of the table driver 60 and the measurement unit driver 70 of the second embodiment, a light shield filter may be arranged above the table 12 and below the measurement unit 200. In this modified example, the light shield filter covers the entire upper portion of the table 12. The light shield filter includes electrically-controlled shutters. The calculation unit 30 sequentially changes the measurement regions A11 to Ann by sequentially opening and closing the shutters. This modified example is referred to as the modified example Z.

The modified example Z may include a filter in which a lattice of liquid, crystal filters change transmitting wavelengths instead of the light shield filter. In this modified example of the foodstuff analysis device 1, for example, when one liquid crystal filter transmits only the first particular wavelengths, other filters are kept from transmitting the first particular wavelengths. Each liquid crystal filter is changed to a state in which only the first to third particular wavelengths are transmitted. When the entire filters are changed to the state in which only the first to third particular wavelengths are transmitted, the portion nutrition information of the entire measurement subject S may be calculated.

In the foodstuff analysis device 1 of the third embodiment, (procedure 24) and (procedure 25) may be omitted. In this case, the calculation unit 30 may form an approximate curve of the graph shown in FIG. 9A and execute an interpolation process for interpolating values of the approximate curve into portions that have not been measured. Alternatively, when an average value of the portion nutrition information of two measurement portions that are adjacent to each other in the graph of FIG. 9A is calculated, an interpolation process may interpolate the average value into the portion that has not been measured.

In the image obtaining unit 27 of the fourth embodiment, the filters that transmit visible light may have only one color. In this case, a single-colored picture image PP is shown on the display 50. The image obtaining unit 27 may have any structure as long as outputs showing the picture image PP based on visible light are obtained. Additionally, the structure may be such that received light amounts of the light reception elements 26 of the light reception sensors 25A to 25C are overlapped. In this case, an image similar to the picture image PP based on the visible light may be displayed. In the structure that uses the received light amounts of the light reception elements 26 of the light reception sensors 25A to 25C, it is preferred that adjacent light reception elements 26 correspond to one portion region PX. In this case, the distribution image P is rough as compared to the picture image PP in which the light reception elements 26 are all pixels. Thus, the user may easily recognize the component distribution.

The calculation unit 30 of the fourth embodiment shows, on the display 50, the superimposed image PS in which the distribution image P is superimposed on the picture image PP. Instead, an image showing the picture image PP through the distribution image P may be shown on the display 50. Alternatively, an image in which a portion of the picture image PP, for example, the outline of the measurement subject S, is replaced by the distribution image P may be shown.

The foodstuff analysis device 1 of the fifth embodiment may further include a mouse that enables a pointer to move in the display 150. The user selects a selected range RS using the mouse. In this case, the touch panel function may be omitted from the display 150. In this modified example, the mouse corresponds to the "selection unit." The selection unit may have any structure as long as the user can select a selected range RS.

The foodstuff analysis device 1 of the fifth embodiment may receive at least one of target calories and target component amounts as the designated information.

The calculation unit 30 of the sixth embodiment may replace portion nutrition information of portions that are not included in the selected range RS with substitute presentation information. In this case, the display 150 shows the components and calories obtained by adding the total nutrition information of the substitute presentation information to the sum of portion nutrition information of portions included in the selected range RS.

The calculation unit 30 of the sixth embodiment may store at least one of the total calories and components of a number of kinds of foodstuff in advance. The calculation unit 30 selects substitute nutrition information from the stored foodstuff information and shows the substitute nutrition information on the display 150.

The calculation unit 30 of the sixth embodiment shows the distribution image P in which the selected range RS is replaced by the foodstuff candidate Cn on the display 150. Additionally, the distribution image P of the foodstuff candidate Cn may be displayed by adding to a portion that is not included in the selected range RS. Further, the components of the foodstuff candidate Cn and the components of the selected range RS may be compared and indicated using a graph, a numeral value, or the like.

The calculation unit 30 of the sixth embodiment shows the foodstuff candidates C1 to Cn on the display 150 when the selected range RS is input but may be changed as follows. If the component amounts of the measurement subject S are less than the target component amounts when the selected range RS is not input, the foodstuff candidates C1 to Cn may be selected based on the difference between the component amounts of the measurement subject S and the target component amounts. Additionally, the foodstuff candidates C1 to Cn may be displayed by adding to the distribution image P.

The calculation unit 30 of the sixth embodiment may calculate the selected range RS and the substitute presentation information based on the difference between the target component amounts and the component amounts of the measurement subject S to show on the distribution image P in which the selected range RS is replaced by the foodstuff candidate.

The calculation unit 30 of the seventh embodiment may be configured to allow the user to input calories that are wished to be decreased from the measurement subject S by a numeral value. In this case, the same process as steps S14 to S18 of the selected range determination process is repeated until the sum of portion calories of portion regions PX selected in step S16 conforms to the input calories.

The configuration of the seventh embodiment may be changed so that each component amount conforms to the target component amount instead of calories.

In the seventh embodiment, the process of steps S15 to S18 may be changed to a process described below. Portion regions PX having portion calories lower than the threshold value are eliminated, and the total calories are divided by the remained potion regions PX, and the number of portion regions PX that conform to the difference between the total calories and the target calories is calculated. Then, the calculated number of portion regions PX is emphasized and displayed on the distribution image P.

In the measurement of the first to seventh embodiments, the emittance of light, from the light source 21 may be performed for a predetermined period.

In the first to seventh embodiments, the number of the particular wavelength reflection units 24 and the light reception sensors 25 may be one, two, four, or more. The particular wavelengths reflected by the particular wavelength reflection unit 24 may be changed to wavelengths that are correlated with calories of a foodstuff or components of a foodstuff.

For example, the calorie coefficient of protein and the calorie coefficient of carbohydrate are the same. Thus, in a configuration for calculating calories, wavelengths that well reflect both protein and carbohydrate may be used to analyze protein and carbohydrate together. In this configuration, the particular wavelength reflection unit 24 may use two reflectors. Even in this configuration, when calories and fat are calculated as portion nutrition information of the measurement subject S, a distribution image P of the calories and fat may be shown on the displays 50, 150.

Water does not affect calories. Thus, the calories of a foodstuff are smaller as the ratio of water contained in the foodstuff increases. Therefore, when the ratio of water is calculated using wavelengths that well reflect water of a foodstuff, the calories may be calculated. In this configuration, the particular wavelength reflection unit 24 may include one reflector. Even in this configuration, when calories are calculated as portion nutrition information of the measurement subject s, the distribution image P of the calories may be shown on the displays 50, 150. Additionally in each embodiment of the foodstuff analysis device 1, the calculated ratio of water may be used to correct fat, protein, carbohydrate, and calories.

The foodstuff analysis device 1 of the first to seventh embodiments analyzes fat, protein, carbohydrate, and calories of the measurement subject S. Instead or additionally, components of water, salt, various minerals, vitamins, or the like may be analyzed, and a distribution image of the components may be displayed. In this case, water, salt, various minerals, and vitamins correspond to "portion nutrition information."

The light reception elements 26 of the first to seventh embodiments may be changed to light reception elements 26 that selectively have the sensitivity to the first to third particular wavelengths. In this case, the reflectors 24A to 24C may be omitted. Additionally, in this modified example, two of the light reception sensors 25A to 25C, 250A to 250C may be omitted. More specifically, one light reception sensor 25, 250 may include sets of light reception elements 26 that are arranged in a lattice and selectively have the sensitivity to the first to third particular wavelengths. The light reception sensor 25, 250 may calculate the portion nutrition information of each measurement portion.

The absorbance wavelength of hydrogen bond changes in accordance with the temperature. Thus, a plurality of particular wavelength reflection units 24 and light reception sensors 25 may be provided for one single wavelength. In this case, the particular wavelength reflection units 24 and the light reception sensors 25 are changed in accordance with the temperature of the measurement subject S.

Figure 18:
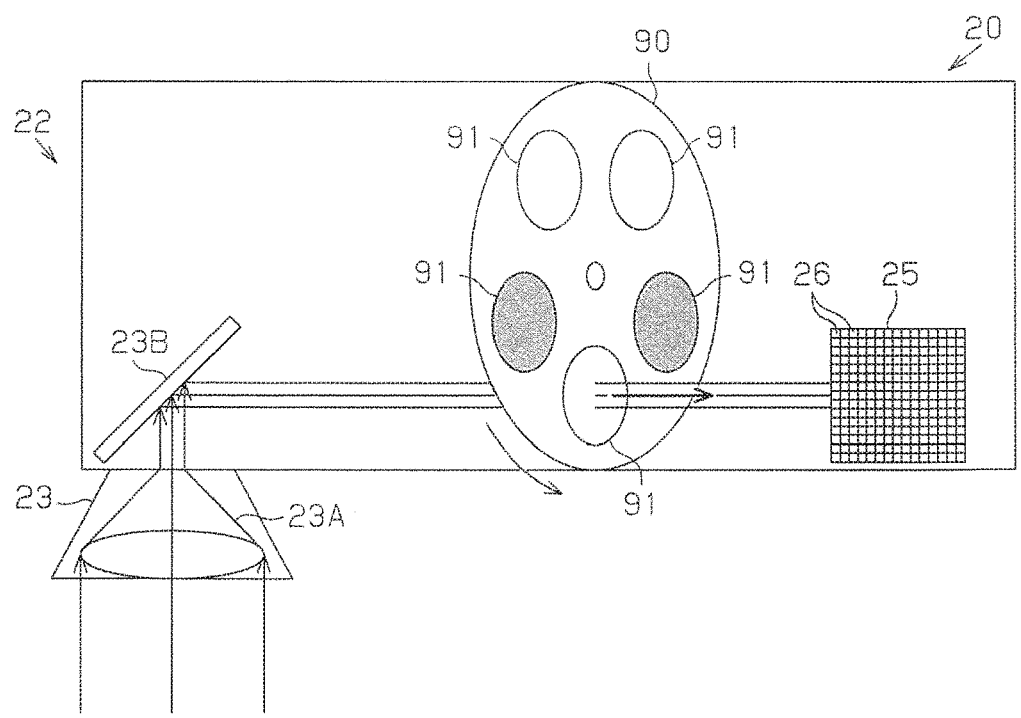
FIG. 18 is a diagram showing the structure of a modified example of the light reception unit of each embodiment.

The measurement units 20, 200 of the first to seventh embodiments may include a filter switching unit 90 shown in FIG. 18. The filter switching unit 90 includes filters 91. The filters 91 only transmit light having particular wavelengths. The light reception sensors 25 including a lattice of the light reception elements 26 are located at the downstream side of the filter switching unit 90. The calculation unit 30 may change the wavelength directed toward the light reception sensors 25A to 25C by changing the filter 91 opposed to the light reception sensors 25. In this modified example, the number of light reception sensors 25 may be reduced as compared to a structure in which light reception sensors 25 are arranged for each set of particular wavelengths. This modified example is referred to as a modified example X.

The modified example X may include a filter capable of changing reflecting particular wavelengths in accordance with applied voltage, for example, an acousto-optic filter, instead of the filter switching unit 90. Alternatively, a Fabry-Pérot interference filter may be used. In this case, the Fabry-Pérot interference filter includes a drive source such as a motor that changes the distance (gap length) between two mirrors included in the interference filter. The change in the gap length changes the wavelength of light transmitting the interference filter.

The modified example X may include a set of three filters that transmit only one of the first to third particular wavelengths to the light reception sensors 25 instead of the filter switching unit 90. The three filters are coupled opposing to three light reception elements 26. The portion nutrition information corresponding to one portion region PX is calculated based on a set of the three light reception elements 26.

In the modified example X, when the filter switching unit 90 is arranged between the light source 21 and the measurement subject S, the wavelengths of light directed toward the light reception sensors 25 may be changed. Alternatively, when a plurality of right sources 21 that emits only particular wavelengths, which may be LEDs or lasers, are used, the wavelengths of light directed toward the light reception sensors 25 may be changed by sequentially changing the light sources 21.

In the modified example X, a reflector the angle of which is changeable may be located at an upstream side of the filter switching unit 90. The light reception sensors 25 are located at a downstream side of each filter 91. When the angle of the reflector is changed, each filter 91 and each light reception sensor 25 are sequentially irradiated with the light reflected from the measurement subject S. This modified example is referred to as a modified example Y.

The modified example Y may include a spectral unit, which disperses light, instead of the reflector. Additionally, the light reception sensors 25 are located at a downstream side of the spectral unit and a position corresponding to a particular wavelength of the dispersed light.

The reflectors 24A to 24C of the measurement units 20, 200 of the first to seventh embodiments may be changed to a configuration that transmits only particular wavelengths. In this case, each light reception sensor 25 is located at a rear side of the corresponding reflectors 24A to 24C.

The measurement unit 20, 200 of the first to seventh embodiments may include a plurality of light sources 21.

The light source 21 may be omitted from the measurement units 20, 200 of the first to seventh embodiments. In this case, the measurement subject. S may be analyzed using light including near-infrared rays such as sunlight or illumination located inside the room where the foodstuff analysis device 1 is located in this case, the case 11 may also be omitted.

Figure 19:
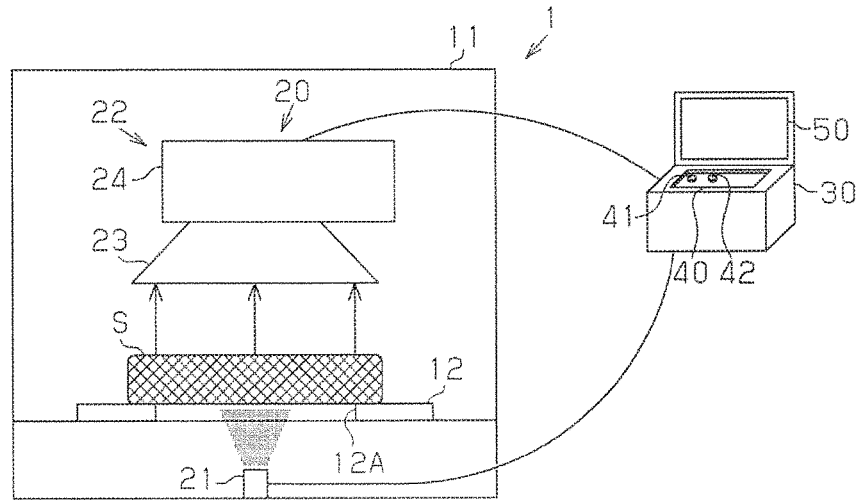
FIG. 19 is a schematic diagram showing the entire structure of a modified example of the foodstuff analysis device of each embodiment.

In the measurement units 20, 200 of the first to seventh embodiments, the light source 21 and the light reception units 22, 220 are located above the measurement subject S. Instead, one of the light source 21 and the light reception units 22, 220 may be located below the measurement subject S. For example, FIG. 19 shows a modified example of the measurement unit 20 in which the light source 21 is located below the table 12. The table 12 includes a window 12A that transmits near-infrared light. The light reception unit 22 receives light that has transmitted through the measurement subject S. Alternatively, when one of the light source 21 and the light reception units 22, 220 is located both above the measurement subject S and below the table 12, the dispersed reflection light and the transmitted light of the measurement subject S are used for the measurement.

The displays 50, 150 of the first to seventh embodiments show the ratio of a component having the largest ratio in each portion region PX on the component distribution image P. However, two components may be simultaneously displayed. In this case, the ratio of each component is indicated by an intermediate color of the presentation colors of two components having larger ratios. As the ratio of one of the two components to the other component increases, the displayed presentation color is closer to the presentation color corresponding to the component.

When a distribution image P showing only the ratio of protein, a distribution image P showing only the ratio of fat, and a distribution image P showing only the ratio of carbohydrate are formed, the configuration may be such that the distribution images P are switched by the switching button 42.

The displays 50, 150 of the first to seventh embodiments show the ratios of the components on the component distribution image P but may show absolute amounts of the components.

The displays 50, 150 of the first to seventh embodiments show the presentation colors having darkness corresponding to the absolute value of calories on the calorie distribution image P. Instead, of the entire portion regions PX, one having the maximum calories may have the darkest presentation color, and one having the minimum calories may have the lightest presentation color. Ones having other calories may be displayed in representation colors having intermediate darkness in a stepped manner.

The displays 50, 150 of the first to seventh embodiments indicate the calorie amounts and the component ratios by the darkness of the presentation colors on the calorie distribution image P and the component distribution image P. Additionally, kinds of component are indicated by different presentation colors. However, brightness, differences in color, and patterns may be used for such indication. Alternatively, a three-dimensional bar chart may be used. Any image may be used as long as the distribution image P allows for visual recognition of portion nutrition information.

The first to seventh embodiments may include a comparison measurement mode. In the comparison measurement mode, the measurement is performed when only a food container, in which the measurement subject S will be placed, or nothing is placed on the table 12. Based on outputs of the light reception elements 26 obtained in the comparison measurement mode, the calculation unit 30 corrects the outputs of the light reception elements 26 or the portion nutrition information. If outputs of the light reception elements 26 obtained when measuring the measurement subject S have the same value as the output of the light reception elements 26 obtained in the comparison measurement mode, the portion nutrition information may be configured not to be shown on the corresponding portion region PX.

The table 12 may include a reference portion where the measurement subject S is not placed. The calculation unit 30 may correct the portion nutrition information based on outputs of the light reception elements 26 corresponding to the reference portion.

Further, in the fifth embodiment, the user may operate the touch panel of the display 150 and select a portion of the distribution image P where the foodstuff is not placed. The calculation unit 30 corrects the portion nutrition information based on outputs of the light reception elements 26 corresponding to the selected portion and shows the corrected portion nutrition information on, the display 150.

The first to seventh embodiments may further include a particular wavelength reflection unit and a light reception sensor that receive only the light having particular wavelengths having a small effect on calories and components and used for correction. The portion nutrition information may be corrected based on an output of a light reception element 26 of the light reception sensor. The particular wavelengths for correction are determined using foodstuffs having known calories and component information. In one example of specific procedures, the measurement is performed in state A in which the measurement subject S is not placed on the table 12, in state B in which only the food container for the measurement subject S is placed on the table 12, and in state C in which the measurement subject S is placed on the table 12. Then, the measurement result of state A is subtracted from the measurement result of state B to obtain a reference, and the reference measurement result is formalized by the particular wavelengths for correction.

Figure 20:
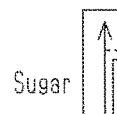
FIG. 20 is a front view showing a modified example of presentation of the display of each embodiment.
Figure 20:
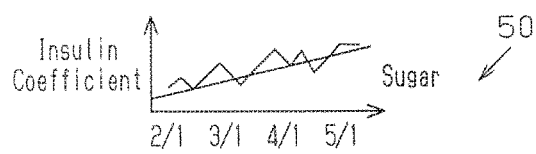

The first to seventh embodiments may include a history memory that stores a measurement result of portion nutrition information of the measurement subject S. In this modified example, contents stored in the history memory may be used, for example, to control the blood sugar value of a diabetic patient. More specifically, as shown in FIG. 20, a list of amounts of sugar calculated from the amount of carbohydrate contained in the measurement subject S (measured sugar amounts) is displayed. Also, necessary amounts of insulin calculated from the measured sugar amounts) are displayed.

In this modified example, when the actual blood sugar value and the intake amount of insulin are input in the foodstuff analysis device 1 using the operation unit 40 or the display 50, 150, the displays 50, 150 may indicate the comparison with the measured sugar amounts as shown in FIG. 20. Further, when an insulin coefficient calculated from the blood sugar value and the intake insulin amount is also displayed, the amount of carbohydrate that should be consumed next time may be calculated as the target component amount.

The first to seventh embodiments may include a history memory that stores the measurement result of the portion nutrition information of the measurement subject S and show a future weight tendency of the user on the displays 50, 150 based on the history. Additionally, a recommended intake value may be displayed based on the weight tendency. For example, when the total calories of the measurement subject S continue to be high relative to the target calories, "weight may increase" may be displayed as the weight tendency. Additionally, when analyzing the measurement subject S, "−200 kcal" may be displayed as the recommended intake value.

In the first to seventh embodiments, the portion nutrition information calculated by the calculation unit 30 may be only one or two of calories, component ratios, component amounts.

In the first to seventh embodiments, the measurement subject S is analyzed when the measuring button 41 is pressed. Instead, the measurement subject S may be repeatedly analyzed in a predetermined time after the measuring button 41 is pressed. In this case, the foodstuff analysis device 1 may also have, for example, a cooking function, and changes in the components during cooking may be displayed.

In the first to seventh embodiments, the portion nutrition information or distribution image information of the measurement subject S may be transmitted to an external device through a network. The external device may control the history of the measurement subject S.

The invention claimed is:

1. A foodstuff analysis device comprising:
a light reception detector that includes a plurality of light reception elements arranged in a lattice, wherein a position of each of the light reception elements corresponds to a position of a corresponding at least one measurement portion of a plurality of measurement portions of a measurement subject, and the light reception detector is configured to receive near-infrared light reflected from the plurality of measurement portions of the measurement subject and near-infrared light transmitted through the plurality of measurement portions of the measurement subject and generates a signal corresponding to a light amount of received light;
a calculation unit that is configured to calculate portion nutrition information for each of the plurality of measurement portions of the measurement subject that indicates calories of at least one measurement portion of the measurement subject based on the signal provided from the light reception detector and form a calorie distribution image throughout the measurement subject by combining each of pieces of portion nutrition information corresponding to the plurality of measurement portions with position information of the corresponding measurement portion, wherein the calorie distribution image includes a plurality of portion regions that are respectively associated with the plurality of measurement portions; and
a display that is configured to show the calorie distribution image provided from the calculation unit.

2. The foodstuff analysis device according to claim 1, further comprising a selection unit that is configured to select a range of a portion of the calorie distribution image as a selected range in accordance with an operation of a user, wherein the calculation unit is configured to form reference information based on pieces of portion nutrition information included in the selected range and shows the reference information on the display.

3. The foodstuff analysis device according to claim 2, wherein the reference information includes information that indicates one of a sum of pieces of portion nutrition information included in the selected range and a sum of pieces of portion nutrition information that are not included in the selected range.

4. The foodstuff analysis device according to claim 2, wherein
the reference information includes substitute presentation information that indicates calories of one or more kinds of foodstuff, and
the calculation unit is configured to:
replace at least one piece of portion nutrition information included in the selected range by the substitute presentation information and show the replacement on the display,
add the substitute presentation information to at least one piece of portion nutrition information that is not included in the selected range and show the addition on the display, or
compare at least one piece of portion nutrition information included in the selected range with the substitute presentation information and show the comparison on the display.

5. The foodstuff analysis device according to claim 1, further comprising an information input unit that is configured to allow a user to input designated info nation, wherein the calculation unit is configured to:
calculate a target value of intake calories based on the designated information,
calculate total nutrition information including entire calories of the measurement subject from the portion nutrition information,
compare the target value and the total nutrition information,
generate suggestion information used for the total nutrition information to be proximate to the target value, and show the suggestion information on the display.

6. The foodstuff analysis device according to claim 1, further comprising a history memory that is configured to store at least one of pieces of portion nutrition information of the measurement subject and the calorie distribution image.

7. The foodstuff analysis device according to claim 1, wherein the light reception detector is one of a plurality of light reception detectors, and
the calculation unit is configured to calculate pieces of portion nutrition information based on signals respectively provided from the pieces of portion nutrition information.

8. The foodstuff analysis device according to claim 1, further comprising a driver that is configured to move at least one of the light reception detector and a light path of near-infrared light received by the light reception detector relative to the measurement subject,
wherein the calculation unit is configured to calculate the portion nutrition information of measurement portions in accordance with the relative movement.

9. The foodstuff analysis device according to claim 1, further comprising a distance detector that is configured to detect a distance to the measurement subject from the light reception detector,
wherein the calculation unit is configured to correct the portion nutrition information based on an output of the distance detector.

10. The foodstuff analysis device according to claim 1, further comprising an image obtaining unit that is configured to capture an image of the measurement subject,
wherein the calculation unit is configured to form image data of the measurement subject based on an output of the image obtaining unit, and
the display is configured to show one of the calorie distribution image superimposed on the image data of the measurement subject and the image data through the calorie distribution image.

* * * * *